United States Patent
Taton et al.

(10) Patent No.: US 9,814,805 B2
(45) Date of Patent: Nov. 14, 2017

(54) COATINGS FOR CONTROLLED RELEASE OF HIGHLY WATER SOLUBLE DRUGS

(71) Applicant: INNOVATIVE SURFACE TECHNOLOGIES, INC., St. Paul, MN (US)

(72) Inventors: Kristin Taton, Little Canada, MN (US); Lawin Laurie, New Brighton, MN (US); Patrick Guire, Hopkins, MN (US)

(73) Assignee: INNOVATIVE SURFACE TECHNOLOGIES, INC., St. Paul, MN (US)

( * ) Notice: Subject to any disclaimer, the term of this patent is extended or adjusted under 35 U.S.C. 154(b) by 0 days.

(21) Appl. No.: 14/786,842

(22) PCT Filed: Apr. 25, 2014

(86) PCT No.: PCT/US2014/035527
§ 371 (c)(1),
(2) Date: Oct. 23, 2015

(87) PCT Pub. No.: WO2014/176545
PCT Pub. Date: Oct. 30, 2014

(65) Prior Publication Data
US 2016/0067385 A1    Mar. 10, 2016

Related U.S. Application Data

(60) Provisional application No. 61/815,910, filed on Apr. 25, 2013.

(51) Int. Cl.
*A61L 29/08*    (2006.01)
*A61L 27/54*    (2006.01)
(Continued)

(52) U.S. Cl.
CPC ............. *A61L 29/085* (2013.01); *A61L 27/34* (2013.01); *A61L 27/54* (2013.01); *A61L 29/06* (2013.01);
(Continued)

(58) Field of Classification Search
CPC .............. A61L 29/06; A61L 2300/104; A61L 2300/206; A61L 2300/602;
(Continued)

(56) References Cited

U.S. PATENT DOCUMENTS

| 5,002,582 A | 3/1991 | Guire et al. |
| 5,271,945 A | 12/1993 | Yoshioka et al. |

(Continued)

FOREIGN PATENT DOCUMENTS

| WO | WO 2004/014447 A1 | 2/2004 |
| WO | WO 2005/099786 A1 | 10/2005 |
| WO | WO 2013/006947 A1 | 1/2013 |

OTHER PUBLICATIONS

International Search Report for corresponding International App. No. PCT/US2014/035527, dated Aug. 25, 2014 (3 pages).

(Continued)

*Primary Examiner* — Aradhana Sasan
(74) *Attorney, Agent, or Firm* — Weaver Legal and Consulting LLC; Karrie Gemignani Weaver

(57) ABSTRACT

The present disclosure relates to multilayer coatings that include a hydrophobic encasing layer and allow controlled release of a water soluble drug. The encasing layer encases water soluble, or hydrophilic, drugs with a flexible layer and comes in good intimate contact with the water soluble drug layer. Thus, the encasing layer conforms to the water soluble drug and can control the release of the drug. Advantageously, major cuts or fissures in the coating do not cause the water soluble drug to leak or burst out; rather, the encasing (Continued)

layer continues to provide modulated release of the drug. The present disclosure also includes methods of making the multilayer coatings, methods of using the multilayer coatings, and articles that include the multilayer coatings.

19 Claims, 3 Drawing Sheets

(51) Int. Cl.
*A61L 31/16* (2006.01)
*A61L 31/10* (2006.01)
*A61L 27/34* (2006.01)
*A61L 29/16* (2006.01)
*A61L 29/10* (2006.01)
*A61L 29/06* (2006.01)

(52) U.S. Cl.
CPC .............. *A61L 29/106* (2013.01); *A61L 29/16* (2013.01); *A61L 31/10* (2013.01); *A61L 31/16* (2013.01); *A61L 2300/104* (2013.01); *A61L 2300/206* (2013.01); *A61L 2300/602* (2013.01); *A61L 2300/608* (2013.01); *A61L 2420/02* (2013.01); *A61L 2420/08* (2013.01)

(58) Field of Classification Search
CPC ........... A61L 2300/608; A61L 2420/02; A61L 2420/08; A61L 27/34; A61L 27/54; A61L 29/085; A61L 29/106; A61L 29/16; A61L 31/10; A61L 31/16
See application file for complete search history.

(56) References Cited

U.S. PATENT DOCUMENTS

| | | |
|---|---|---|
| 5,714,360 A | 2/1998 | Swan et al. |
| 6,099,562 A | 8/2000 | Ding et al. |
| 6,120,536 A | 9/2000 | Ding et al. |
| 6,278,018 B1 | 8/2001 | Swan |
| 7,544,673 B2 | 6/2009 | DeWitt et al. |
| 7,828,789 B2 | 11/2010 | Tanaka et al. |
| 8,034,369 B2 | 10/2011 | Anderson et al. |
| 8,142,836 B2 | 3/2012 | Chappa |
| 8,163,034 B2 | 4/2012 | Chang et al. |
| 8,361,052 B2 | 1/2013 | Tremblay |
| 8,496,954 B2 | 7/2013 | Chappa et al. |
| 2004/0220665 A1 | 11/2004 | Hossainy et al. |
| 2005/0100577 A1 | 5/2005 | Parker et al. |
| 2011/0159072 A1 | 6/2011 | Missling et al. |
| 2011/0223212 A1 | 9/2011 | Taton et al. |
| 2012/0100187 A1 | 4/2012 | Chappa et al. |
| 2012/0258313 A1 | 10/2012 | Wen et al. |
| 2012/0302950 A1 | 11/2012 | Landsman et al. |
| 2014/0178447 A1* | 6/2014 | Modak .................. A61L 29/02 424/407 |

OTHER PUBLICATIONS

Extended European Search Report for corresponding European App. No. 14 78 8719, dated Feb. 27, 2017 (12 pages).

* cited by examiner

COATINGS FOR CONTROLLED RELEASE OF HIGHLY WATER SOLUBLE DRUGS

CROSS REFERENCE TO RELATED APPLICATIONS

This application claims benefit under 35 U.S.C. §119(e) to U.S. Patent Application Ser. No. 61/815,910, entitled "RELEASE COATINGS FOR HIGHLY WATER SOLUBLE DRUGS," filed 25 Apr. 2013, the contents of which are incorporated herein in their entirety.

FIELD

Inventive concepts relate generally to release of highly water soluble drugs from multilayer coatings. This disclosure also relates to methods for producing and using these multilayer drug release coatings.

BACKGROUND

Generally speaking, the field of drug delivery can be described as encompassing approaches, formulations, technologies and systems for transporting a pharmaceutical compound in the body to achieve one or more desired therapeutic effects. Drug delivery techniques may involve systemic administration and/or site-specific delivery of one or more drugs within the body. In order to achieve the desired therapeutic effect(s), systemic and site-specific approaches typically take into account both quantity and duration of drug presence.

Drug delivery may involve release of drug from a surface of a medical article, for example, release of drug from a coating provided on a surface of a medical article. In these aspects, drug delivery techniques can be concerned with modulating the release profile of a drug from such coatings to achieve a desired dosage of the drug. Delivery of hydrophilic drugs can present challenges. Drug elution rates for a coating containing a hydrophilic or lipophilic drug are typically very fast initially when the article contacts body fluid or blood. This is the so-called "burst effect." Multilayer coatings that include a topcoat over drug containing layers have been used to control release of drugs. However, small defects in coatings, including cracks, abrasions and cuts, or even water absorption by the topcoat, can lead to rapid burst release of hydrophilic drugs. As such, it is difficult to design coatings which stably entrap or encase a water soluble drug and allow controlled release of the water soluble drug over periods of days or weeks.

SUMMARY

Generally speaking, the present disclosure relates to coatings that include multiple coating layers. Inventive multilayer coatings include an encasing layer that allows controlled release of a water soluble drug. The encasing layer is unique in that it encases water soluble, or hydrophilic, drugs with a flexible layer and comes in good intimate contact with the water soluble drug layer. Thus, the encasing layer conforms to the water soluble drug and can control release of the drug. Advantageously, major cuts or fissures in the coating do not cause the water soluble drug to leak or burst out; rather, the encasing layer continues to provide modulated release of the drug.

In one embodiment, a drug eluting article may include a substrate, a primer layer disposed on the substrate, a hydrophilic drug layer comprising a highly water soluble drug disposed on the primer layer, and a hydrophobic encasing layer disposed on the hydrophilic drug layer. The primer may include a polymer, one or more latent reactive groups that are pendent from the polymer, and one or more noncovalent linking groups, the noncovalent linking groups selected to interact with the substrate. In some implementations, the hydrophobic encasing layer may include the polymer of the primer layer.

In another embodiment, and as illustrated in FIG. 1, a drug eluting article (10) of the disclosure may include a substrate (4), a primer layer (3) disposed on the substrate, a hydrophilic or water soluble drug layer (2) disposed on the primer layer, and a hydrophobic or alkane soluble encasing layer (1) disposed on the hydrophilic or water soluble drug layer.

In other embodiments, a drug eluting article may include a substrate, a water soluble drug layer comprising a highly water soluble drug disposed on the substrate, and a $C_5$-$C_{12}$ alkane soluble encasing layer disposed on the hydrophilic drug layer.

In yet another embodiment, and as illustrated in FIG. 2, a drug eluting article (20) of the disclosure may include a substrate (4), a hydrophilic or water soluble drug layer (2) disposed on the substrate, and a hydrophobic or alkane soluble encasing layer (1) disposed on the hydrophilic or water soluble drug layer.

Also contemplated are methods of making and using the encasing layer, and articles that include the encasing layer. Thus, a further embodiment includes a method, the method including disposing a primer layer on a substrate, curing the primer layer, coating an aqueous solution of a highly water soluble drug onto the primer layer to form a highly water soluble drug layer, and coating a non-aqueous solution of an encasing polymer onto the highly water soluble drug layer to form an encasing layer.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
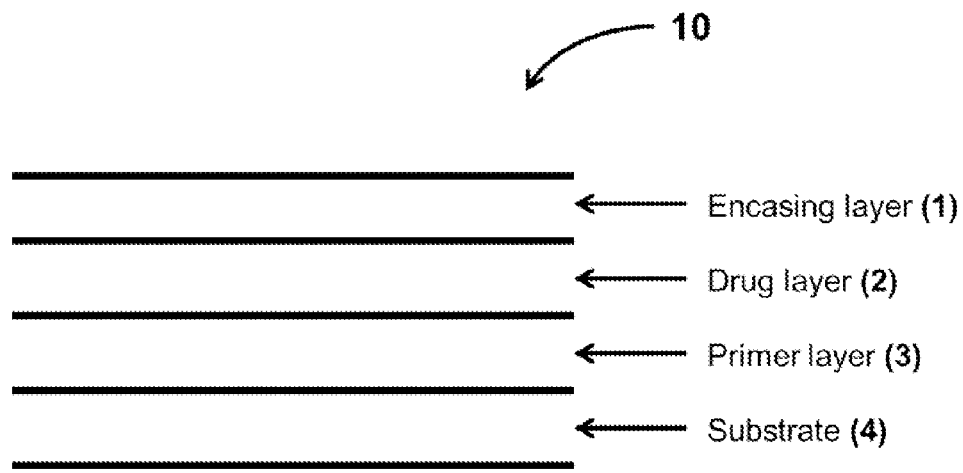
FIG. 1 is a schematic diagram of an illustrative drug eluting article.

In a general sense, the present disclosure relates to multilayer coatings that allow controlled release of a water soluble drug. It is particularly difficult to design coatings which stably entrap or encase a water soluble drug and also allow controlled release of the water soluble drug. The multilayer coatings of the disclosure as described herein, which allow controlled release of a water soluble drug, include an "encasing layer." The encasing layer is unique in that it encases water soluble, or hydrophilic, drugs with a flexible layer and comes in good intimate contact with the water soluble drug layer. Further, the encasing layer when applied to a medical article also conforms to the article and interacts favorably with placement devices and tunneling and insertion techniques when applicable. Thus, the encasing layer conforms to the water soluble drug and can control the release of the drug through thickness, formulation, or both from at least 1-2 days through several weeks or months.

Advantageously, major fissures, cuts or breaches to the coatings do not cause the water soluble drug to leak or burst out; rather, the encasing layer continues to provide controlled release of the drug. In many embodiments, the multilayer coating is flexible and does not interfere with bulk material properties such as elongation, flexibility or torsion of the medical article. The present disclosure also includes methods of making the coating, methods of using the coating, and articles that include the coating. While the present disclosure is not so limited, an appreciation of the various aspects of this disclosure will be gained through a discussion of the embodiments provided below.

All scientific and technical terms used herein have meanings commonly used in the art unless otherwise specified. The definitions provided herein are to facilitate understanding of certain terms used frequently herein and are not meant to limit the scope of the present disclosure.

In accordance with inventive concepts, multilayer coatings are contemplated that can provide controlled release of a hydrophilic drug that is contained within the multilayer coating. Inventive coatings are thus composed of two or more coating layers; i.e., at least a hydrophilic drug layer and a hydrophobic encasing layer. Optionally, a primer layer may be included. To prepare the multilayer coatings, coating compositions (e.g., solutions) are prepared that include the desired agent (for example, hydrophilic drug, encasing polymer, and, optionally primer polymer). The coating compositions are then applied to a substrate, forming coated layers. The word "layer," as used herein, will refer to a coating of sufficient dimensions (such as thickness and coverage area) for its intended use (such as over all, or a portion) of a substrate. A layer is an amount of a distinct coating composition that is disposed on a surface. Each distinct coating composition can be applied to a substrate or layer in one or more applications to achieve the desired amount of that coating composition on that substrate or layer.

As used herein, when an element, component or layer for example is described as being "on" or "disposed on" another element, substrate or layer, it can be directly on or intervening elements, substrates or layers may be on the particular element, substrate or layer, for example. When an element, substrate or layer for example is referred to as being "directly on" another element, substrate or layer there are no intervening elements, substrates or layers, for example.

The term "hydrophobic" refers to any molecule or solute that is "very slightly soluble," "practically insoluble," or "insoluble" in water. Very slightly soluble means that from about 1000 to 10,000 parts solvent, for example, are needed to dissolve 1 part solute. Practically insoluble means that more than 10,000 parts solvent, for example, are needed to dissolve 1 part solute. Insoluble means that a solute is unable to dissolve in water.

The term "hydrophilic" refers to a solute that is at least "slightly soluble" in water. Slightly soluble means that about 100 to 1000 parts solvent, for example, are needed to dissolve 1 part solute. Hydrophilic may also refer to a solute that is at least "sparingly soluble," at least "soluble," at least "freely soluble," or at least "very soluble" in water. Sparingly soluble means that about 30 to 100 parts solvent, for example, are needed to dissolve 1 part solute. Soluble means that about 10 to 30 parts solvent, for example, are needed to dissolve 1 part solute. Freely soluble means that about 1 to 10 parts solvent, for example, are needed to dissolve 1 part solute. Very soluble (also referred to herein as "highly soluble") means that less than 1 part solvent is needed to dissolve 1 part solute.

The term "aqueous solution" refers to any solution containing a hydrophilic solute dissolved in water. The term "non-aqueous solution" refers to any solution containing a hydrophobic solute dissolved in a solvent other than water.

One purpose of this disclosure is to enable controlled elution of a drug from an article. To accomplish this the disclosure describes multilayer coatings that include an encasing layer which allows the controlled release of a drug from the coatings. As used herein, "controlled release" refers to release of a drug into a patient's body at a desired dosage (including dosage rate and total dosage) and duration of treatment. For example, the particular formulation of the multilayer coating (including the amounts and ratios of the individual components of the coating) can be selected to achieve a desired release profile of the drug. The release profile can include the amount of drug released from the coating per unit time. Generally speaking, release kinetics of drug in vivo are believed to include both a short term ("burst") release component, and a longer term release component. As used herein, the modulation (acceleration or deceleration) of drug release can include either or both of these release kinetics components.

Thus, in accordance with inventive concepts, drug elution kinetics are controlled in a manner to meet a particular therapeutic application. As described herein, "elution" of a drug includes any process of release that involves extraction or release of the drug by contact of the material with bodily fluids. Inventive concepts provide controlled elution of one or more drugs to provide a desired elution rate profile of the drug(s).

In one embodiment, as illustrated in FIG. 1, a drug eluting article (10) of the disclosure may include a substrate (4), a primer layer (3) disposed on the substrate, a hydrophilic or water soluble drug layer (2) disposed on the primer layer, and a hydrophobic or alkane soluble encasing layer (1) disposed on the hydrophilic or water soluble drug layer. In many embodiments the hydrophilic or water soluble drug layer (2) is substantially free of a binder material.

The ability to coat a hydrophilic drug onto a medical article without using a binder material to control release of that hydrophilic drug from the medical article surface is a unique aspect of inventive concepts that provides advantages over conventional techniques.

As used in conventional techniques, a binder material can comprise a material that is combined with a drug (for example, mixed with or otherwise formulated with the drug) to enhance retention of the drug within a coating layer or matrix. More specifically, binder material can be mixed with drug to formulate a distinct coating composition that is deposited on a surface as a coating layer. A binder material can comprise one or more polymers selected to enhance retention of the drug within a coating or matrix. For example, binder material comprising a polymeric matrix can be combined with drug to provide a binder/drug coating composition that is deposited on a surface. Within the binder/drug coating layer, the binder may entrap drug within the matrix and thereby retain the drug within the matrix and on a substrate surface. Such retention can comprise physical retention (e.g., entrapment) and/or chemical retention (e.g., by chemical interaction between the drug and polymeric matrix). An example of polymeric matrices that can retain drug through such interactions include biodegradable polymers (for example that can release drug as they degrade or erode), swellable polymers (that can release drug upon swelling), polymers that include hydrolysable linkages (that release drug upon hydrolysis), and the like. Thus, even conventional multilayer coatings that include drug will provide a polymeric coating layer that is composed of a polymer combined with drug (for example, the drug can be dispersed or otherwise mixed with the polymer, or even coupled to a polymeric component).

In contrast to conventional techniques that utilize binder material to retain drug, inventive concepts do not require binder material. In accordance with inventive concepts, the hydrophilic or water soluble drug layer serves as a reservoir of drug for elution from a multilayer coating. The ability to use a water soluble drug layer that is substantially free of binder material can provide unexpected features. As contemplated herein, a water soluble drug layer is substantially free of a binder material if there is an insignificant amount of binder material in the layer, for example, less than 5% wt, or less than 4% wt, or less than 3% wt, or less than 2% wt, or less than 1% wt of a binder material, based on the total weight of the water soluble drug layer. Stated another way, in many aspects, the drug layer is composed predominantly of, or entirely of, hydrophilic drug. For example, the water soluble drug layer can contain drug in an amount of about 95% wt or greater, or 96% wt or greater, or 97% wt or greater, or 98% wt or greater, or 99% wt or greater.

The ability to include drug at these high levels can provide important benefits, for example, as the amount of hydrophilic drug that is available to a patient following administration of the drug-containing coatings can be maximized. Further, inventive concepts can simplify formulation of drug release coatings, since the hydrophilic drug(s) are not mixed with binder material (and thus consideration of compatibility of the drug and binder material, including suitable solvents, is not of concern). Because inventive coatings do not contain binder, these multilayer coatings can be thinner, and bulk properties of the underlying medical article are more likely retained.

In some aspects, inventive concepts provide drug eluting articles that include a hydrophilic drug layer comprising a highly water soluble drug disposed on the primer layer, wherein the hydrophilic drug layer is not composed of drug that is dispersed or interspersed in a binder material.

It is surprising that the drug alone can be solely applied as a simple aqueous solution of drug and water, since it would be expected that the drug would require a binder material in order to adhere to the substrate. Surprisingly, inventive coatings that include a hydrophilic drug layer comprising an aqueous solution of drug provide controlled elution of the drug from the coatings. Such features can be observed even in the event the multilayer coatings are compromised, for example, by cuts or fissures.

The coatings of the instant disclosure can be provided to a wide variety of substrates. In some aspects, the multilayer coatings can be utilized in connection with substrates that are otherwise difficult to coat. In some embodiments, the substrate is a medical article. The encasing layer is flexible and can therefore be advantageous for use with a medical article since it may not interfere with bulk material properties such as elongation, flexibility, and torsion as many drug releasing coatings can.

When used in connection with medical articles, inventive coatings can be applied to medical articles fabricated from a wide variety of materials. Suitable materials useful to fabricate medical articles include, without limitation, metals, minerals or ceramics, fabrics, composites, carbon-based materials, and polymers.

Suitable metals include, for example, aluminum, chromium, cobalt, iron, tantalum, titanium, and alloys thereof, as well as nitinol and other nickel-titanium alloys, and stainless steels. Examples of suitable minerals or ceramics include alumina, hydroxyapatite, quartz, sapphire, silica and glasses. Illustrative carbon-based materials include pyrolytic carbon, as well as carbon materials obtained by thermal degradation (thermolysis, pyrolysis) or organic compounds.

Inventive coatings can be particularly useful in connection with medical articles fabricated of silicone (poly(dimethylsiloxane)). In further aspects, inventive concepts can be used in connection with a number of other polymer materials. Illustrative synthetic polymers include Parylene™ (trade term for a variety of chemical vapor deposited poly (p-xylylene) polymers), polyamides (such as polyether block amides such as PEBAX™), polyesters, polyethylenes, polyethylene terephthalate (PET), poly(meth)acrylates, polyacetates, polyvinylacetates, sulfonic acid-substituted polymers, polyacrylamide polyethylene glycols, polyethyleneimines, polylactic acids, polyglycolic acids, polylactide-co-glycolides, polyvinyl alcohols, polyvinyl pyrrolidones, quaternary amine-substituted polymers, conductive polymers (for example, polyvinylpyridine, polyacetylenes, polypyrroles), poly-(p-phenyleneterephthalamides), polyphosphazenes, polypropylenes, polytetrafluoroethylenes, polysiloxanes, inorganic synthetic elastomers, organic polymers, or copolymers thereof or combinations of any of these.

In some embodiments, the coatings of this disclosure are applied to a substrate formed from natural polymers such as polysaccharides, proteins, nucleic acids or organic polymers.

Medical articles can include implantable devices, such devices intended to be placed within a patient for a short or extended period of time. Thus, in some implementations, inventive concepts can be applied to substrates that are intended to function in contact with tissue and/or fluids of the body. Additionally, medical articles can include devices that are in contact with tissue and/or fluids of the body and yet not implanted in the body (non-implanted).

Illustrative implantable medical articles include, but are not limited to, vascular devices such as guidewires, stents, stent grafts, covered stents, catheters (single use and long-term), valves, distal protection devices, aneurysm occlusion devices, septal defect closures; cardiac devices such as artificial hearts and heart assist devices such as defibrillators, pacemakers and pacing leads; orthopedic devices such as joint implants and fracture repair devices; dental devices such as dental implants and repair devices; ocular devices and glaucoma drain shunts; urological devices such as penile, sphincter, urethral, bladder and renal devices; synthetic prostheses such as breast prostheses and artificial organs; surgical closures; laparoscopic fixation devices; endosurgical components; tracheal, esophageal or bronchial tubes; ear tube components; fixation devices (plates, screws, tacks, pins, nails); shunts; dialysis components; filters; ports; sensors; scaffolds; patches; and the like. In some implementations, the medical article is a catheter, such as a silicone catheter.

Non-implanted medical articles can be provided with inventive coatings as well, including such articles as transdermal drug delivery devices (such as patches, bandages, dressings, and the like); dialysis devices and associated tubing, catheters, membranes and grafts; autotransfusion devices; vascular and surgical devices including a wide variety of catheters (atherectomy, angiographic, clot extraction, angioplasty, electrophysiology, and the like), intraaortic balloon pumps, intracardiac suction devices, blood pumps, blood oxygenator devices (including tubing and membranes), blood filters, blood temperature monitors, hemoperfusion units, plasmapheresis units, transition sheaths, dialators, intrauterine pressure devices, breathing circuit connectors, stylets (vascular and non-vascular), guidewires (coronary, peripheral, and the like); dialators (e.g., urinary, etc.); surgical instruments (e.g., scalpels and the like); endoscopic devices (such as endoscopic surgical tissue extractors, esophageal stethoscopes); and general medical and medically related devices including blood storage bags, umbilical tape, membranes, wound dressings (including bandages), wound management devices, needles, percutaneous closure devices, transducer protectors, uterine bleeding patches, clamps, cannulae; as well as diagnostic slides (such as oligonucleotide arrays, microarrays, protein chips and fluorescence in situ hybridization (FISH) slides); chromatographic support materials; cell culture devices; biosensors; and the like.

In some implementations, one or more primer layers can be included in inventive drug eluting medical articles. When included, primer layers can be useful for facilitating adhesion between the substrate and another element, substrate or layer. Generally, the presence of a primer layer can improve adherence of a coating layer onto a substrate. Preferably, the primer layer is disposed directly on the substrate.

In many embodiments, the primer layer includes a priming agent comprising polymer, one or more latent reactive groups that are pendent from the polymer, and one or more noncovalent linking groups, wherein the noncovalent linking groups are selected to interact with the substrate to which the priming agent is applied. In some implementations, a priming agent can be disposed on the substrate, and the noncovalent linking group(s) can act to associate with the substrate. External energy can be applied to the coated substrate to activate the latent reactive group(s) and, in some cases, form a covalent bond between the priming agent itself and the substrate. Thus, both the noncovalent linking group(s) and the latent reactive group(s) interact with the substrate surface.

In accordance with inventive aspects, the priming agent comprises one or more polymers. As used herein, a "polymer" is a compound formed by covalently linking smaller molecules termed "monomers." The monomers present in a polymer molecule can be the same or different. If the monomers are different, the polymer also may be called a copolymer. The polymer component of the priming agent can serve as a backbone for attachment of non-covalent linking groups, latent reactive groups, or both non-covalent linking groups and latent reactive groups. In these aspects, the non-covalent linking groups, the latent reactive groups, or both the non-covalent linking groups and the latent reactive groups can be described as being "pendent" from the polymer. In turn, the "polymer backbone" of the priming agent can be identified as the polymer without inclusion of pendent non-covalent linking groups and/or latent reactive groups. A polymer can be obtained from a commercial source or be synthesized from the polymerization of a desired monomer or combination of different monomers. Methods of polymer synthesis are well known in the art.

A wide variety of polymers can be used in the priming agent of the disclosure. Suitable polymers for use in the priming agent include, without limitation, synthetic polymers (such as silicones and silicone rubbers), and derivatives, copolymers, or combinations, blends or mixtures of polymers. In some embodiments, the polymer included in the priming agent of the disclosure includes a polymaleic acid derivative. Preferably, the polymaleic acid is a derivative of a copolymer such as poly(alkene-co-maleic acid). In some embodiments, the polymaleic acid derivative is a derivative of a copolymer including alternating polyolefin and poly(maleic anhydride). Preferably, the alternating copolymer includes about 50 mole % polyolefin and about 50 mole % poly(maleic anhydride). Any of the polymers described in U.S. Publication No. US 2012/0258313 A1 (Wen et al., "Coating Agents and Coated Articles," published 11 Oct. 2012) can be used.

The priming agent also includes one or more latent reactive groups that are pendent from the polymer. The latent reactive group(s) can be chosen such that they are compatible with the substrate to be primed or coated. Compatibility includes, but is not limited to, the latent reactive group reacting with the substrate upon being subjected to activation energy. Covalent bonding of the coating agent to the substrate can occur through the activation of the latent reactive groups of the coating agent.

The latent reactive group can be a photoreactive group or thermoreactive group that can become chemically reactive when exposed to an appropriate energy source. In some implementations, the latent reactive group can be a photoreactive group. As used herein, the phrases "latent photoreactive group" and "photoreactive group" are used interchangeably and refer to a chemical moiety that can be sufficiently stable to remain in an inactive state (ground state) under ambient storage conditions but that can undergo a transformation from the inactive state to an activated state when subjected to appropriate reaction conditions. Similarly, the phrases "latent thermally reactive" and "thermoreactive group" can be used interchangeably and in the same sense. For such latent reactive groups, appropriate reaction conditions may include exposure to an external energy source. Suitable external energy sources include light sources (such as UV or ultraviolet light) or heat sources. Other illustrative reaction conditions may include chemical reaction conditions, for example, the presence of oxidizers and reducing agents (redox pairs).

Generally, photoreactive groups respond to specific applied external stimuli to undergo active specie generation with resultant covalent bonding to an adjacent chemical structure, for example, as provided by the same or a different molecule. Suitable photoreactive groups are described, for example, in U.S. Pat. No. 5,002,582 (Guire et al.).

Photoreactive groups can be chosen to be responsive to various types of actinic energy. Typically, groups are chosen that can be photoactivated using either ultraviolet or visible radiation. Suitable photoreactive groups include, for example, aryl ketones, azides, diazos, diazirines, ketones, and quinones. The photoreactive groups generate active species such as free radicals including, for example, nitrenes, carbenes, and excited states of ketones upon absorption of electromagnetic energy.

In some implementations, the photoreactive group can be an aryl ketone, such as acetophenone, benzophenone, anthrone, and anthrone-like heterocycles (heterocyclic analogs of anthrone such as those having N, O, or S in the 10-position), or their substituted (for example, ring-substituted) derivatives. Examples of aryl ketones include heterocyclic derivatives of anthrone, including acridone, xanthone, and thioxanthone, and their ring substituted derivatives. Other suitable photoreactive groups include quinones such as, for example, anthraquinone.

Illustrative azides include arylazides such as phenyl azide and 4-fluoro-3-nitrophenyl azide; acyl azides (—CO—$N_3$) such as benzoyl azide and p-methylbenzoyl azide; azido formates (—O—CO—$N_3$) such as ethyl azidoformate and phenyl azidoformate; sulfonyl azides (—$SO_2$—$N_3$) such as benzenesulfonyl azide; and phosphoryl azides $(RO)_2PON_3$ such as diphenyl phosphoryl azide and diethyl phosphoryl azide.

Illustrative diazo compounds include diazoalkanes (—$CHN_2$) such as diazomethane and diphenyldiazomethane; diazoketones (—CO—$CHN_2$) such as diazoacetophenone and 1-trifluoromethyl-1-diazo-2-pentanone; diazoacetates (—O—CO—$CHN_2$) such as t-butyl diazoacetate and phenyl diazoacetate; and beta-keto-alpha-diazoacetates (—CO—$CN_2$—CO—O—) such as t-butyl alpha diazoacetoacetate. Diazo compounds are also thermally reactive groups.

Other photoreactive groups include diazirines (—$CHN_2$) such as 3-trifluoromethyl-3-phenyldiazirine, and ketenes (CH=C=O) such as ketene and diphenylketene.

Photoreactive groups can be non-ionic or ionic. Illustrative non-ionic photoreactive groups include the tetrakis (4-benzoylbenzyl ether) or the tetrakis (4-benzoylbenzyl ester) of pentaerythritol. Illustrative ionic photoreactive groups are discussed in US 2012/0258313 A1 (Wen et al.), U.S. Pat. No. 6,278,018 (Swan) and U.S. Pat. No. 5,714,360 (Swan et al).

In some implementations, latent reactive group(s) can comprise one or more thermally reactive groups. Thermal activation may be advantageous when exposure to UV light is not practical (for example for the inner lumen of a tubular medical article) or is undesirable (for example when coating materials contain UV light-sensitive components). Thermally reactive groups can also be advantageous in coatings exhibiting low transmission of UV light.

Thermally reactive groups can include pairs of atoms having a heat sensitive (labile) bond between the atoms. Examples of such pairs of atoms include oxygen-oxygen (per-esters and peroxides), nitrogen-oxygen, and nitrogen-nitrogen. Examples of thermally reactive groups useful in present embodiments include 4,4' azobis(4-cyanopentanoic acid) and analogs of benzoyl peroxide. External energy sources to produce thermal energy can be used to activate a thermally reactive group.

In some embodiments, the latent reactive group can include one or more nitrenogenic groups. For example, a latent reactive group can comprise a perhalophenylazide (PHPA), such as perfluorophenylazide (PFPA). Perfluorophenylazides typically can be derived from 4-azido-2,3,5,6-tetrafluorobenzoic acid. A "nitrenogenic group" is a chemical moiety that becomes a nitrene group when exposed to a reaction-energy source. An azido group is an example of a nitrenogenic group. In turn, a "nitrene group" (also generally termed "nitrene" or "nitrene intermediate") is a particular form of nitrogen group regarded as the nitrogen analog of carbenes. Like carbenes, nitrenes are generally regarded as intermediates that are highly reactive and may not be isolatable under ordinary conditions. Important nitrene reactions include, but are not limited to, addition or insertion in C—H, N—H, O—H, and C—C bonds (single and double).

In some implementations, the latent reactive groups can comprise chemical reactive groups. Suitable chemical reactive groups can be referred to as redox initiators, redox catalysis agents, or redox activation agents. In general, combinations of organic and inorganic oxidizers, and organic and inorganic reducing agents are used to generate radicals for polymerization. A description of redox initiation can be found in *Principles of Polymerization*, $2^{nd}$ Edition, Odian G., John Wiley and Sons, pages 201-204 (1981), that part of which is herein incorporated by reference.

Photoinitiator groups and thermally activated initiator groups that utilize energy that is not damaging to biological systems can also be used. In an embodiment, photoinitiator groups having long wavelength UV and visible light-activated frequencies are coupled to the backbone of the polymer. In other embodiments, visible light-activated photoinitiators can be pendent to the polymer.

Covalent bonding of the priming agent to the substrate can occur through the activation of the latent reactive groups of the priming agent. The priming agent can be exposed to a reaction energy source, such as light or thermal energy, to activate the latent reactive groups, thereby promoting formation of a coating on the substrate. In some embodiments, the latent reactive group preferably includes a photoreactive group that can become chemically reactive when exposed to an appropriate energy source (such as UV or ultraviolet light). In other embodiments, the latent reactive groups can comprise a thermally reactive group that can become reactive when exposed to an appropriate energy source (such as heat sources).

The priming agent also includes noncovalent linking groups selected to interact with the substrate. Selection of noncovalent linking groups for a particular priming agent can thus take into account such factors as the substrate to be coated, other components of the priming agent to be utilized (such as the polymer and latent reactive group(s) to be included in the priming agent), solvent systems, reaction conditions and the like. The priming agent is particularly advantageous for facilitating adhesion to articles comprising silicone rubber. Thus, in embodiments where the substrate includes silicone, the noncovalent linking groups of the priming agent may include silicone affinity groups.

In accordance with inventive aspects, noncovalent linking groups can be selected to provide an advantageous interaction, association, attraction, or an affinity with a substrate. The term "non-covalent linking group" is a phrase that characterizes the occurrence of an interaction, attraction or affinity with the substrate and moieties on or in embodiments of the priming agent. The non-covalent linking group can interact with the substrate during contact of the substrate with the non-covalent linking group, or when the non-covalent linking group is brought within sufficient proximity to a substrate.

Illustrative non-covalent linking groups include silane groups, siloxane groups, carboxyl groups, quaternary amine groups, polyamides, $C_4$-$C_{20}$ alkyl groups, polyethylene glycol, acrylates, polyacrylates, polyurethanes, polycarbonates, polyesters, polyethylenes, polypropylenes and polyethers. In some implementations, the non-covalent linking group can comprise a lipophilic group. In further embodiments, the non-covalent linking group can be the reaction product of 3-aminopropylmethylbis(trimethylsiloxy)silane with the anhydride group of poly(maleic anhydride-alt-1-octadecene) to form a pendent amide siloxane group represented by the following formula:

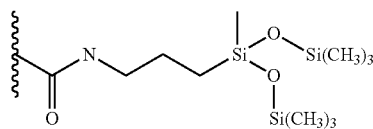

(I)

wherein wavy lines represent the polymer.

In some implementations, a non-covalent linking group can comprise a catechol-based group that is capable of interacting with a surface. One illustrative example comprises catecholamine (that is, dopamine, or 4-(2-aminoethyl) benzene-1,2-diol).

In some aspects, interaction of the non-covalent linking group and the substrate can be independently attributed to many different factors. By example, some of the factors independently contributing to the interaction of the non-covalent linking group with the substrate include, but are not limited to, (i) charge-charge interactions (such as between an amine group and a sulfonate group, for example); (ii) hydrogen binding interactions; (iii) dipole interactions (such as between carbonyl groups, for example); (iv) fluctuating dipole interactions (such as the interaction between aromatic groups or between hydrocarbon groups, for example); (v) counter ion effects; and (vi) hydrophobic/hydrophilic interactions.

Preferred priming agents for use in the instant disclosure are disclosed in U.S. Patent Application Publication 2012/0258313 A1 (Wen, et al.), which is incorporated by reference herein in its entirety.

Advantageously, the primer layer may also increase the durability of the drug layer. As used herein, the term "durability" refers to the wear resistance of a coating, or the ability of the drug layer to be maintained on a substrate surface when subjected to forces typically encountered during use (for example, normal force, shear force, and the like). A more durable drug layer is less easily removed from a substrate by abrasion. Durability of a drug layer can be assessed by subjecting a substrate (such as a medical device) to conditions that simulate use conditions as is demonstrated in Example 4.

In accordance with inventive concepts, multilayer coatings comprise a hydrophobic encasing layer, and features of this component will now be described. The encasing layer of the instant disclosure includes a polymer. Useful polymers for the encasing layer of this disclosure are hydrophobic and may also be referred to herein as encasing polymers. Examples of useful classes of hydrophobic encasing polymers are well known and can include, for example, polyisobutylene, polybutylmethacrylate, poly(maleic anhydride), polyolefin, polybutadiene, polyisoprene, a polystyrene block copolymer, a polystyrene block polyolefin copolymer, and derivatives, combinations and/or copolymers thereof. As used herein, a "derivative" refers to the groups attached to the backbone of the polymer.

Generally, any hydrophobic encasing polymer can be used in the encasing layer described herein. In some aspects, the polymer of the encasing layer includes poly(maleic acid) or derivatized poly(maleic anhydride). In some embodiments, the encasing layer polymer is a copolymer including alternating polyolefin and poly(maleic anhydride). Preferably, the alternating copolymer includes about 50 mole % polyolefin and about 50 mole % poly(maleic anhydride). The weight average molecular weight ($M_w$) of the hydrophobic encasing polymer of the encasing layer is preferably in the range of about 30,000 $M_w$ to about 4,500,000 $M_w$. In many embodiments, the hydrophobic encasing polymer of the encasing layer exhibits a $M_w$ of at least 1,000,000. In one embodiment, the hydrophobic encasing layer includes polyisobutylene. Preferably, the encasing layer includes polyisobutylene having a $M_w$ of at least 1,000,000. In an alternative embodiment, the hydrophobic encasing layer includes a polystyrene block copolymer.

The encasing layer is preferably at least soluble in an organic solvent. A solution containing a solute dissolved in an organic solvent may also be referred to as a non-aqueous solution. In some embodiments, the organic solvent is an alkane solvent. Non-limiting examples of alkanes (saturated hydrocarbons having the formula $C_nH_{2n+2}$) include linear alkanes such as methane ($CH_4$), ethane ($C_2H_6$), propane ($C_3H_8$), butane ($C_4H_{10}$), pentane ($C_5$-$C_{12}$), hexane ($C_6H_{14}$), heptane ($C_7H_{16}$), octane ($C_8H_{18}$), nonane ($C_9H_{20}$), decane ($C_{10}H_{22}$), undecane ($C_{11}H_{24}$), dodecane ($C_{12}H_{26}$), and hexadecane ($C_{16}H_{34}$); and branched alkanes such as 2-methyl butane, 2-methylpentane, 2,4-dimethylpentane, 3-methylpentane, and the like. Cycloalkanes ($C_nH_{2n}$) can also be used, such as cyclohexane, cylcopentane, and the like. Alkanes are commonly referred to by the number of carbons; e.g., pentane is the $C_5$ alkane, hexane is the $C_6$ alkane, heptane is the $C_7$ alkane, and so on. In certain embodiments, the encasing layer is at least soluble in a $C_5$-$C_{12}$ alkane. Preferably, the encasing layer is at least soluble in a $C_6$ or $C_7$ alkane.

In some implementations, the encasing polymer comprises the polymer of the priming agent. In these aspects, then, the polymer backbone included in the primer layer and the polymer backbone included in the hydrophobic encasing layer are the same. In some embodiments, the polymer of the priming agent and the encasing polymer comprise a poly (maleic anhydride) derivative. Optionally, the encasing polymer can further comprise one or more noncovalent linking groups. When included, suitable noncovalent linking groups include those described herein with respect to the priming agent. Optionally, the encasing polymer can further comprise one or more latent reactive groups that are pendent from the polymer. When included, suitable latent reactive groups include those described herein with respect to the priming agent. In still further implementations, encasing polymer comprises the polymer of the priming agent, one or more latent reactive groups that are pendent from the polymer, and one or more noncovalent linking groups.

Thus, in some implementations, inventive concepts provide drug eluting articles comprising (a) a substrate; (b) a primer layer disposed on the substrate, the primer comprising a polymer, one or more latent reactive groups that are pendent from the polymer, and one or more noncovalent linking groups, the noncovalent linking groups selected to interact with the substrate; (c) a hydrophilic drug layer comprising a highly water soluble drug disposed on the primer layer; and (d) a hydrophobic encasing layer disposed on the hydrophilic drug layer, the encasing layer comprising the polymer of the primer layer, wherein the encasing layer does not include latent reactive groups. In some implementations, inventive concepts provide drug eluting articles comprising (a) a substrate; (b) a primer layer disposed on the substrate, the primer comprising a polymer, one or more latent reactive groups that are pendent from the polymer, and one or more noncovalent linking groups, the noncovalent linking groups selected to interact with the substrate; (c) a hydrophilic drug layer comprising a highly water soluble drug disposed on the primer layer; and (d) a hydrophobic encasing layer disposed on the hydrophilic drug layer, the encasing layer comprising the polymer of the primer layer, wherein the encasing layer does not include noncovalent linking groups.

The encasing layer may include polymer at an amount of about 5 to about 100 mg/ml in the organic solvent. In embodiments where more than one polymer is included in the encasing layer, each polymer may be present in an amount of about 5 to about 100 mg/ml in the organic solvent. Exemplary encasing layer formulations are set forth in Example 5.

The encasing layer of the disclosure is unique in that it encases the water soluble, or hydrophilic, drug layer with a flexible layer that comes in good intimate contact with the water soluble drug. The encasing layer of the present disclosure is particularly useful for eluting a water soluble drug and is therefore preferably applied over a layer of water soluble drug.

Figure 2:
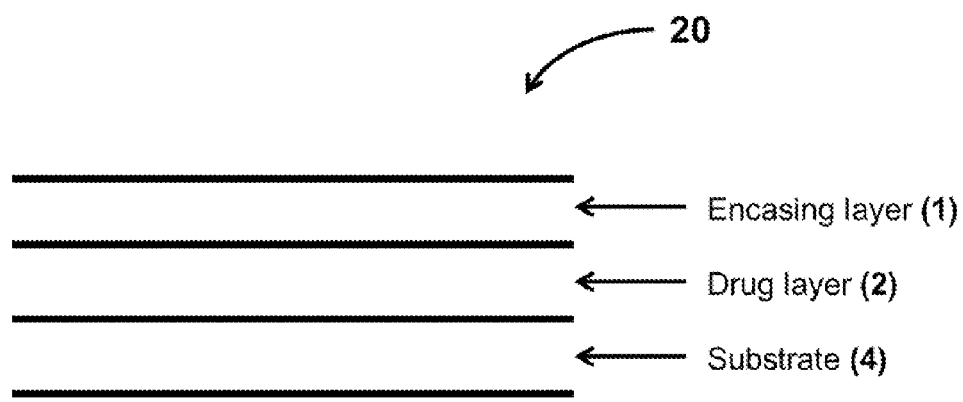
FIG. 2 is a schematic diagram of another illustrative drug eluting article.
Figure 3:
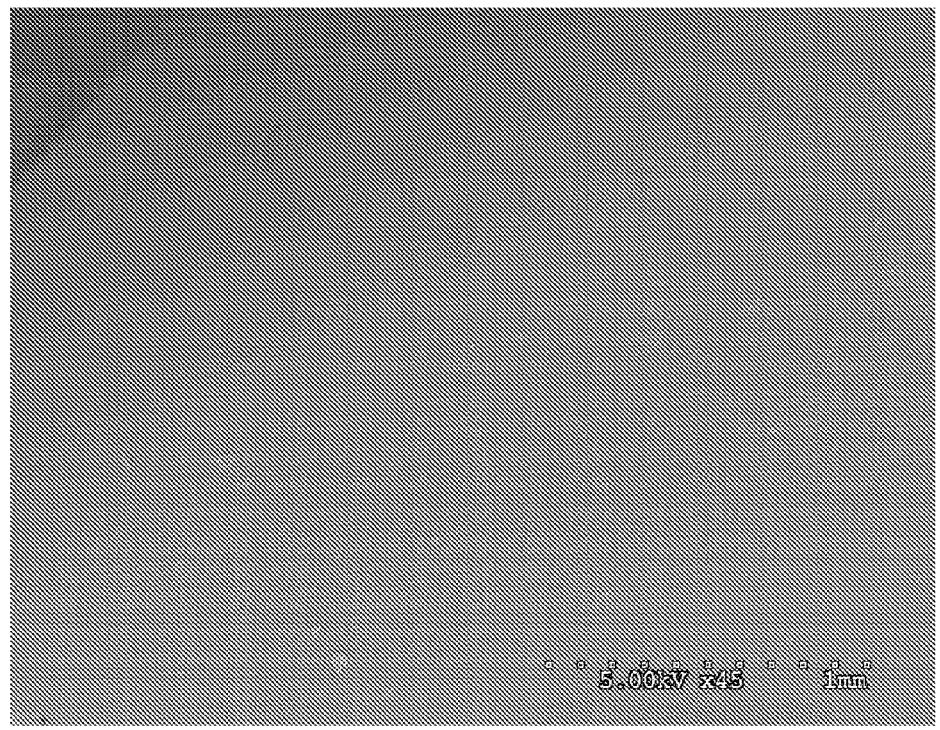
FIG. 3 is an SEM photograph of a top-down view of a primer layer disposed on a silicone rubber article.
Figure 4:
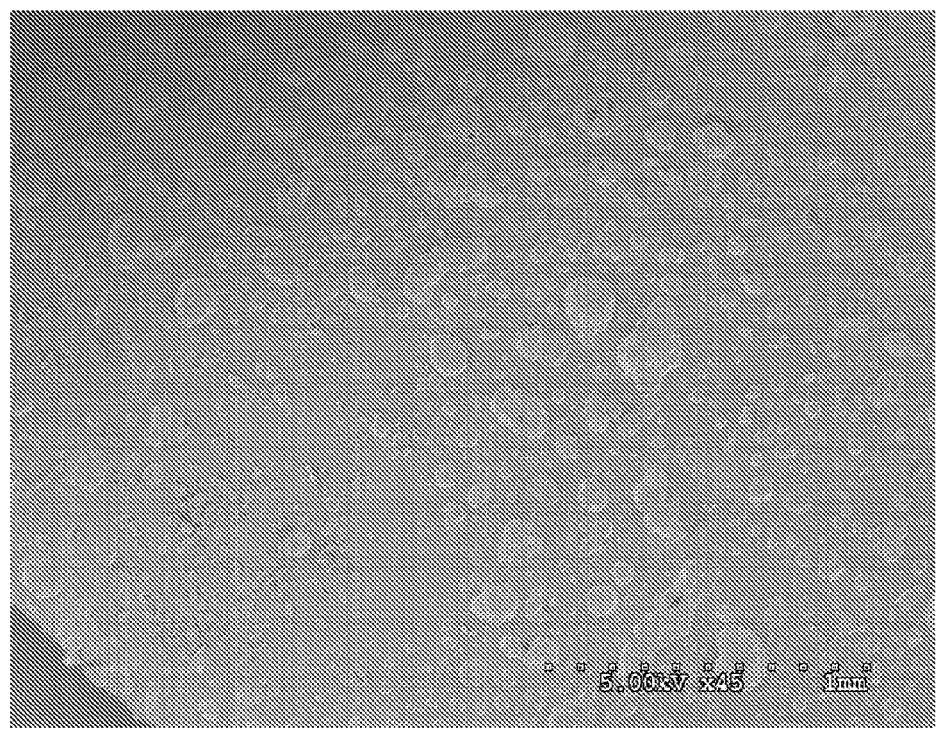
FIG. 4 is an SEM photograph of a top-down view of a layer of silver nitrate disposed on a primer disposed on a silicone rubber article.
Figure 5A:
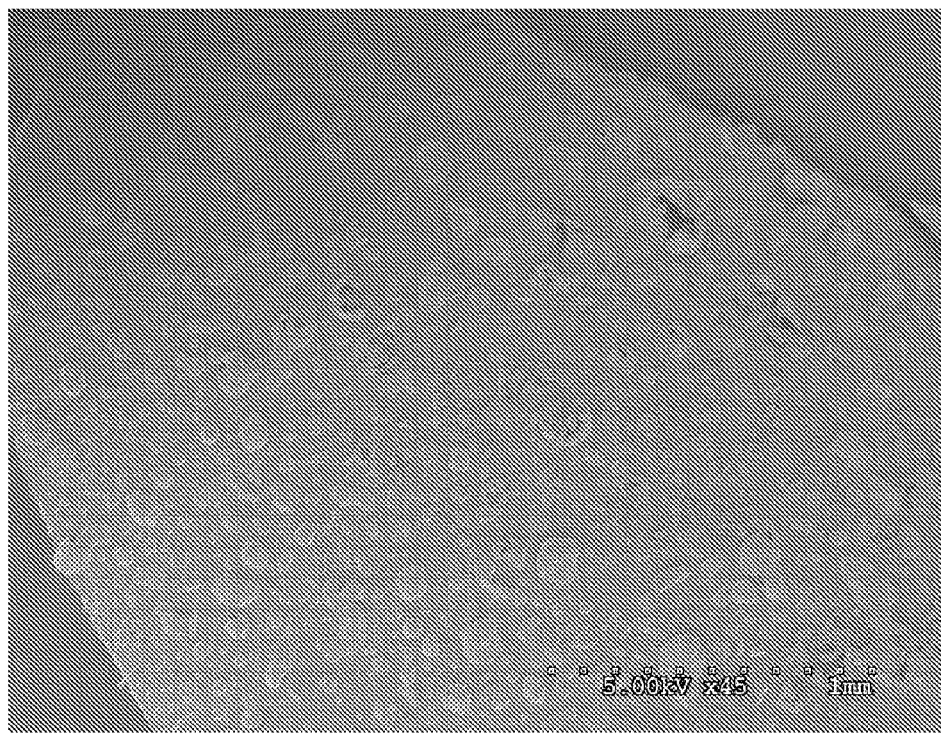
FIG. 5A is an SEM photograph of a top-down view of an encasing layer disposed on a layer of silver nitrate disposed on a primer disposed on a silicone rubber article.
Figure 5B:
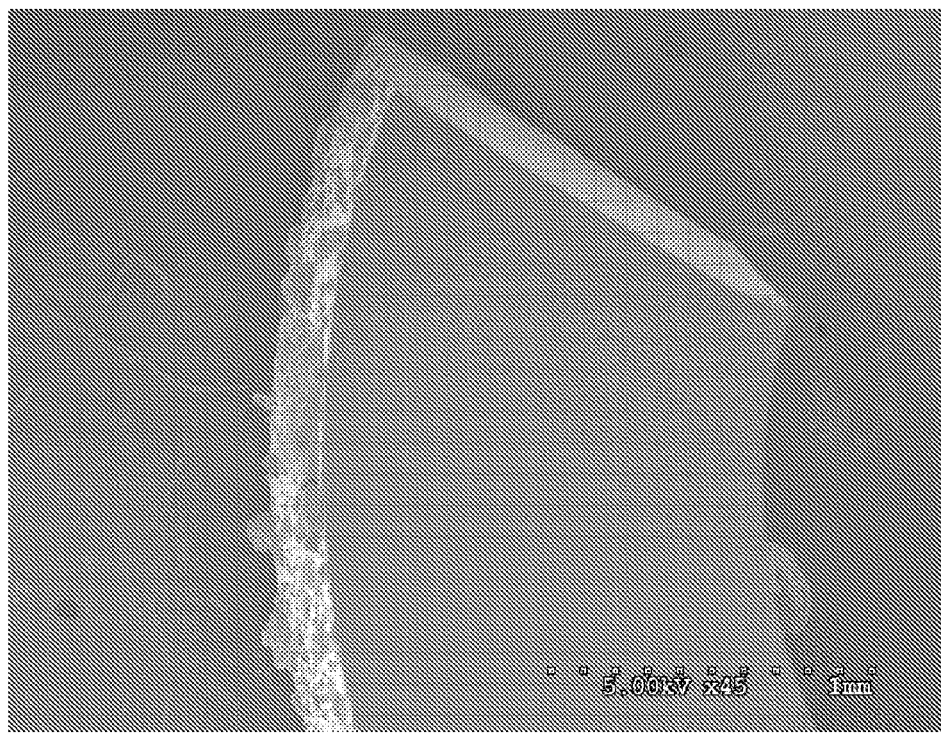
FIG. 5B is an SEM photograph of cross-section view of an encasing layer disposed on a layer of silver nitrate disposed on a primer disposed on a silicone rubber article.

In another embodiment, and as illustrated in FIG. 2, a drug eluting article (20) of the disclosure may include a substrate (4), a hydrophilic or water soluble drug layer (2) disposed on the substrate, and a hydrophobic or alkane soluble encasing layer (1) disposed on the hydrophilic or water soluble drug layer. Suitable formulations for the substrate, hydrophilic or water soluble drug layer, and hydrophobic or alkane soluble encasing layer are disclosed herein. In these embodiments, a primer layer is omitted. In some aspects, the hydrophobic or alkane soluble encasing layer comprises a $C_5$-$C_{12}$ alkane soluble encasing layer. Optionally, the drug eluting article may further include a primer layer disposed between the substrate and the water soluble drug layer. Primer compositions may be any composition as set forth in this disclosure. For example, the primer may include a polymer, one or more latent reactive groups that are pendent from the polymer, and one or more noncovalent linking groups, the noncovalent linking groups selected to interact with the substrate. A preferred primer may include a polymer comprising a polymaleic acid derivative, one or more latent reactive groups comprising photoreactive groups, and noncovalent linking groups comprising siloxane groups.

Inventive multilayer coatings are useful to control release of hydrophilic drugs. As will be understood by a person of skill in the art, a hydrophilic drug is one that has polar groups that enables it to interact with or be dissolved by water and other polar substances. Thus, the terms water soluble drugs and hydrophilic drugs may be used interchangeably herein.

Any highly water soluble drug may be used in the drug layer of the instant disclosure. The highly water soluble drug may be organic or inorganic. The term water soluble drug, as used herein, also includes pharmaceutically useful salts, including, but not limited to silver salts such as silver nitrate. Other useful water soluble drugs may include physiologically active polypeptides, antimicrobials (including antibacterials, antifungals, antivirals, antiparasitics), antitumor agents, antipyretics, analgesics, antiphlogistics, antitussive and expectorant agents, sedatives, muscle relaxants, antiepileptics, antiulcer agents, antidepressants, antiallergic agents, cardiotonics, antiarrhythmic agents, vasodilators, hypotensive diuretics, antidiabetic drugs, anticoagulants, hemostatics, antitubercular agents, hormone preparations, narcotic antagonists, schlerotics, anti-foulings, and anti-infectives. Highly water soluble drugs can form highly concentrated aqueous solutions which, advantageously, allow high concentrations of drug to be loaded on the substrate.

The water soluble drugs of this disclosure are at least "soluble" in water (i.e., only 10 to 30 parts solvent are needed to dissolve 1 part solute). Preferably, the water soluble drugs of this disclosure are "very soluble" in water (i.e., less than 1 part solvent is needed to dissolve 1 part solute). An exemplary, very soluble drug is silver nitrate; 1 gram of water can dissolve over 2 grams of silver nitrate within minutes.

In some implementations, the water soluble drugs of this disclosure can be less than "slightly soluble" in organic solvents (i.e., more than 100 to 1000 parts solvent are needed to dissolve 1 part solute). In such cases, the encasing layer of the instant disclosure, which is at least soluble in an organic solvent, can exhibit very low solubility with the water soluble drug layer of the instant disclosure.

It will be understood upon review of this disclosure that any highly water soluble drug in accordance with the discussion herein can be utilized in the inventive multilayer coatings. Inventive concepts thus provide multilayer coatings, articles, methods and systems that can be utilized with a wide variety of highly water soluble drugs.

In some embodiments, the encasing polymer is present in at least a substantially equal weight amount as the hydrophilic drug. The weight ratio of grams of encasing polymer to grams of hydrophilic drug is at least 0.7:1.0, at least 0.85:1.0, at least 1:1, or at least 2:1, or at least 2.5:1. In some embodiments, the hydrophilic drug is present in a weight ratio of grams of encasing polymer to grams of hydrophilic drug of no more than 10:1. In other embodiments, the weight ratio of grams of encasing polymer to grams of hydrophilic drug is in a range of about 1.2:1 to about 2.5:1.

Embodiments of the invention include methods for applying or forming a coating on a substrate. An exemplary method may include disposing a primer layer on a substrate, curing the primer layer, coating an aqueous solution of a water soluble drug onto the primer layer to form a water soluble drug layer, the water soluble drug having a first weight value, coating a non-aqueous solution of an encasing polymer onto the water soluble drug layer to form an encasing layer, the encasing layer having a second weight value. It is surprising that the drug alone can be solely applied as a simple aqueous solution of drug and water because it would be expected that the drug would require a binder material in order to adhere to the substrate. It is also surprising that the encasing layer alone is able to modulate the release of the highly water soluble drugs. Advantages of this construction include a higher loading level of drug within the multilayer coating. Additionally, simple in-process drug loading determination methods can be utilized.

In many embodiments, the primer layer coatings are conveniently applied onto the substrate as a solution. Suitable solvents compatible with the priming agent are also disclosed in U.S. Patent Application Publication 2012/0258313, which is incorporated by reference herein in its entirety. Illustrative solvents include alkanes, isopropyl alcohol, ketones, chloroform, alcohols, tetrahydrofuran, ethyl acetates, methyl acetates, water, dioxanes, ethers, toluene, petroleum ethers, and mixtures thereof. Primer layer coatings in accordance with inventive concepts can be applied by a standard dip method. A selected medical article may be cleaned prior to application of the primer coating. Briefly, a substrate is immersed in a coating composition containing the priming agent (polymer, latent reactive group, and noncovalent linking group) for a suitable time and then dried to remove remaining solvent. In embodiments where the primer coating includes photoreactive groups, the coated substrate may be cured by UV-irradiation. More specifically, the article may be inserted (i.e., "dipped") into the primer solution, dwelled in the solution, extracted from the primer solution, and air dried at room temperature as is described in Example 1. Other useful coating application methods include spraying, brushing, dabbing, and electrostatic deposition.

In many embodiments, the water soluble drug layers are conveniently applied onto the substrate as an aqueous solution. This aqueous solution can be (surprisingly) free of, or substantially free of a binder material. Water soluble drug layers described in this disclosure are preferably applied by any spray method. Aqueous solutions of highly soluble drug can be used for loading high concentrations of drug on the substrate. This drug solution can be spray coated onto the article as described in Example 1. Once coated, the article can be air dried at ambient or elevated temperature. Other coating application methods include dipping, brushing, dabbing, and electrostatic deposition.

Application of the aqueous drug layer of this disclosure can provide a number of advantages. For example, water soluble drugs can be highly concentrated in aqueous solutions and can thus provide a higher concentration of substantially uniform drug loading on the substrate that cannot be achieved by other methods. In addition, the higher concentration of drug can be loaded with less spray time. Further, spray coating prevents the formation of drug concentration gradients and boluses that can result from, for example, dip methods.

In most embodiments, the hydrophobic encasing layer is applied over a water soluble drug layer. Preferably, the encasing layer is disposed directly on the drug layer. The encasing layer coatings are conveniently applied onto the water soluble drug layer as a solution or dispersion in an application solvent that is not soluble with and will therefore not alter the water soluble drug layer. One method of application for the encasing layer solution is to dipcoat by inserting the article into an encasing layer solution, extracting the article, and drying the article at an ambient or elevated temperature. Another method of application for the encasing layer is a spray coating process. This disclosure offers several benefits that contribute to its ease of use. While other topcoating techniques require spray coating, the encasing layer of this disclosure can be applied by either spray coating or dip coating. Additionally, the hydrophobic encasing layer coatings are not soluble with the hydrophilic drug layer and will therefore not alter the drug layer. In some implementations, the use of coating layers that are not soluble with each other can maintain the distinct chemical composition of each coating layer.

Surprisingly, the encasing layer provides controlled release of the drug from the water soluble drug layer. The encasing may control the release of the drug through thickness, formulation, or both from at least 1-2 days through several weeks or months. Thicknesses of layers can be determined using the Landau-Levich equation:

$$h = 0.94 \frac{(\eta \cdot v)^{2/3}}{(\gamma_{LV})^{1/6}} (\rho \cdot g)^{1/2};$$

where h=thickness, $\gamma_{LV}$=liquid-vapor surface tension, $\eta$=viscosity, g=gravity, $\rho$=density, and V=extraction velocity. Both viscosity and extraction velocity correlate to dip coating thickness by a power of ⅔ and these variables are inversely related for achieving a particular thickness. For example, using a lower viscosity solution with faster extraction may yield a layer of substantially equal thickness to using a higher viscosity solution with slower extraction. A person of skill in the art would understand that any variable may be adjusted in order to achieve a suitable layer thickness.

Advantageously and unexpectedly, cuts or fissures to inventive multilayer coatings do not cause the water soluble drug to leak or burst out; rather, inventive multilayer coatings can continue to provide controlled release of drug even when the coatings are thus compromised. Small defects in conventional coatings, including cracks, abrasions and cuts, or even water absorption by a polymeric topcoat, can lead to rapid burst release of hydrophilic drugs. As demonstrated in Example 6, layers of hydrophilic drug, in the absence of any topcoat, are eluted from the substrate typically in a matter of minutes. However, application of the encasing layer coating of the instant disclosure over a water soluble drug layer is unique in that it encases the water soluble drug layer with a flexible encasing layer that comes in good intimate contact with water soluble drug layer and controls release of the drug. The encasing layer coating conforms to the water soluble drug layer and can control the elution of the drug through thickness and formulation as described herein. Even substantial cuts or cracks to the coating do not cause the hydrophilic drug to burst out; to the contrary, inventive multilayer coatings can continue to provide controlled release of hydrophilic drug even when the coatings are breached or compromised. As can be seen in Example 7, the encasing layer coating effectively encases the drug even after extensive puncturing/slicing of the coating.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The terms "comprises" and variations thereof do not have a limiting meaning where these terms appear in the description and claims.

As used in this specification and the appended claims, the term "or" is generally employed in its sense including "and/or" unless the content clearly dictates otherwise.

"Include," "including," or like terms means encompassing but not limited to, that is, including and not exclusive.

It should be noted that "top" and "bottom" (or other terms like "upper" and "lower") are utilized strictly for relative descriptions and do not imply any overall orientation of the article in which the described element is located.

The present disclosure is illustrated by the following examples. It is to be understood that the particular examples, materials, amounts, and procedures are to be interpreted broadly in accordance with the scope and spirit of the disclosure as set forth herein.

EXAMPLES

The present disclosure will be further explained in greater detail by the examples that follow; however, the scope of this disclosure is not construed to be limited by the scope of these examples.

In the Examples, the reagent referred to as "Photo-POMAS" (photo-poly(octadecene-alt-maleic anhydride)silane) was prepared as described in Example 1 of US Publication No. 2012/0258313 A1, "Coating Agents and Coated Articles," Wen et al., 11 Oct. 2012. The reagent is commercially available from Innovative Surface Technologies, Inc. (St. Paul, Minn.).

Example 1. General Coating Procedures

A. Primer Layer:

Silicone catheters (OD 0.5 mm) were dip coated with 30 mg/ml of a solution of Photo-POMAS in isopropanol. Initially, the silicone rubber was cleaned by rubbing six times with isopropanol with a lint-free cloth. Then, the catheters were inserted into coating solution at a rate of 2 cm/sec, dwelled in the solution for 30 seconds, and extracted from the coating solution at 0.5 cm/sec. The primer coating was air dried for 10 minutes at room temperature, then UV illuminated for one minute with 254 nm light (40 mW/cm$^2$).

B. Silver nitrate Layer:

An aqueous solution of silver nitrate was prepared by dissolving 20 grams silver nitrate (USP grade, 99.8-100.2%, Sigma Aldrich, St. Louis, Mo.) in 10 ml of distilled water. This silver nitrate solution was spray coated on primer coated pieces with a low volume low pressure EFD 7856-46SS sprayhead with Valvemate 2000 (Nordson EFD, East Providence, R.I.). 80 psi backing pressure was used, with a nozzle stroke setting of 13.5. The catheter was fixtured horizontally on a spinning mandrel with a spin rate of 8.5 rpm and the spray head was moved via an ExactaCoat xyz plotter (Sonotek Corp, Milton, N.Y.) at 1.5 mm/sec along the length of the catheter, 26 cm, at a distance of 0.5 inches above the catheter. The silver nitrate aqueous solution was fed into the spray valve via a syringe pump at 0.2 ml/min, while protected from light with aluminum foil. Once coated, the catheter was removed from the mandrel and air dried hanging vertically, protected from light for 24 hours at room temperature.

C. Encasing Layer:

A solution of 30 mg/ml polyisobutylene ($M_W$ 4.2 million, BASF Ludwigshafen, Germany) and 10 mg/ml Photo-POMAS in hexane was prepared. Catheters coated with silver nitrate were dipcoated in the polyisobutylene:Photo-POMAS solution by inserting at 2 cm/sec, then immediately extracting at 0.5 cm/sec and air drying overnight at room temperature.

Example 2. Slow Elution of Silver Nitrate

Elution solution was made by adding 20 ml of ionic strength adjuster (sodium nitrate solution, Orion 940011, ThermoFisher Scientific, Waltham, Mass.) to 1 L of distilled water, then adding 0.03 g of sodium bicarbonate. A catheter coated as described in Example 1 with 89.9 mg of total silver nitrate was placed in 150 ml of this elution solution in a capped 500 ml Erlenmeyer flask at 37° C. with 50 rpm orbital shaking. The elution solution was exchanged daily and the silver content of each elution change was measured with a silver ion selective electrode (Orion IonPlus Silver/Sulfide Electrode, ThermoFisher Scientific, Waltham, Mass.) and meter (Orion Star 214 pH/ISE meter, ThermoFisher Scientific, Waltham, Mass.). Table 1 shows the resulting silver content in mg/L of silver ion.

TABLE 1

| Daily measurement | Day | | | | | | | | |
|---|---|---|---|---|---|---|---|---|---|
| | 0.01 | 1 | 2 | 3 | 4 | 5 | 7 | 9 | 10 |
| mg/L Ag ion | 16.1 | 86.4 | 40.9 | 17.1 | 17.5 | 16.3 | 16.3 | 23.8 | 5.36 |
| mg AgNO$_3$ | 3.8 | 20.4 | 9.6 | 4.0 | 4.1 | 3.9 | 3.9 | 5.6 | 1.3 |
| Cumulative % AgNO$_3$ eluted | 4.2 | 26.9 | 37.7 | 42.2 | 46.8 | 51.1 | 55.3 | 61.6 | 63 |

Example 3. Silver Nitrate Loading

Primer coated pieces coated as in Example 1 were weighed in triplicate, then coated with silver nitrate as described in Example 1 with varying nozzle stroke volumes. After overnight drying, the catheters were weighed again in triplicate. Table 2 contains weights showing varying applications of silver nitrate depending on nozzle width. A second coat of silver nitrate could be applied, repeating the conditions in Example 1B. Weights following overnight drying at room temperature are also shown in Table 2.

TABLE 2

| Spray Parameters | First coat | Second coat, additional AgNO$_3$ wt |
|---|---|---|
| 1200 mg/ml AgNO$_3$, 13 stroke volume, spin rate 7.5, 1.75 mm/sec movement | 34.1 ± 0.5 mg | 42.0 ± 0.3 mg |
| 2000 mg/ml, 13.5 stroke volume, spin rate 12, 1.5 mm/sec movement | 93.8 ± 0.1 mg | — |
| 2000 mg/ml, 13.8 stroke volume, spin rate 12, 1.5 mm/sec movement | 128.3 ± 0.2 mg | — |

Example 4. Adhesion Promotion by Primer Layer

Silicone rubber catheters were coated with silver nitrate as described in Example 1B with and without the primer layer (Example 1A). The two catheters were compared for adhesion of the silver nitrate by simultaneously rubbing the coated silver nitrate catheters along a nitrile gloved hand for a length of 26 cm, repeated three times. The loss of silver nitrate coating could be detected as a white powder on the nitrile gloves for the unprimed samples, but not the primed sample. Loss of weight is shown in Table 3. Results illustrate coatings that included a primer layer provided a more durable coating (no loss of silver nitrate with abrasion) as compared to coatings that lacked a primer layer.

TABLE 3

| | Weight prior to silver nitrate coating | Weight after silver nitrate coating | Weight after abrasion | Loss of silver nitrate due to abrasion |
|---|---|---|---|---|
| Primed silver nitrate catheter | 6.6891 g | 6.8186 g 129.5 mg silver nitrate | 6.8189 | −0.3 mg (gain) |
| Unprimed silver nitrate catheter | 6.7767 g | 6.9064 g 129.7 mg silver nitrate | 6.8934 g | 12.7 mg |

Example 5. Encasing Layer Formulations

Various encasing layer formulations were compared as follows. Silver nitrate coated catheters with primer layer as described in Example 1A/1B were coated with various encasing layers under the conditions of Example 1C. The encasing layers listed in Table 4 were combinations of the following polymers: polyisobutylene ($M_W$ 4.2 and 1.0 million from BASF, Ludwigshafen, Germany), polybutylmethacrylate ($M_W$ 337,000 Sigma Aldrich, St. Louis, Mo.), Photo-POMAS, and polystyrene block-poly (ethylene-ran-butylene)-block polystyrene ($M_W$ 89,000 Sigma Aldrich, St. Louis, Mo.). The encasing layers were subjected to slow elution as in Example 2 with the results in Table 4.

Example 6. Coating without Encasing Layer

A catheter sample was made as described in Example 1, without encasing layer. This sample contained 99.4 mg silver nitrate as determined by weighing the catheter before the silver nitrate layer and after coating and drying. Weights were done in triplicate. The catheter was immersed in 100 ml of elution solution described in Example 1 for 3 minutes at room temperature at 100 rpm on an orbital shaker. The resulting solution was measured to contain 615 mg Ag+/L by silver ion selective electrode; this corresponds to 97.2 mg silver nitrate. Effectively all silver nitrate was released from the coated catheter without encasing layer upon immersion in water within 3 minutes.

Example 7. Encasing Layer Durability

A coated catheter sample was made as described in Example 1 with an encasing layer consisting of the following three polymers: 20 mg/ml polyisobutylene ($M_W$ 4.2 million, BASF Ludwigshafen, Germany), 20 mg/ml polystyrene-block-poly(ethylene-ran-butylene)-block-polystyrene (Sigma Aldrich, St. Louis, Mo.), and 5 mg/ml Photo-POMAS. The catheter contained 110.7 mg of silver nitrate. The catheter was cut lengthwise in half and chopped into 1 cm wide pieces to give 54 small pieces of catheter with coating.

To observe elution from the catheter pieces, the pieces were then placed in 100 ml of elution solution described in Example 1 for 10 minutes at room temperature at 150 rpm on an orbital shaker. After the elution period, the resulting solution was measured by silver ion selective electrode to contain 147 mg Ag+/L, or only 21% of the total silver nitrate content. Results indicated the coating effectively encased the drug even after extensive puncturing/slicing of the coating.

Example 8. Chlorhexidine Gluconate on Mylar Substrate

Mylar pieces were coated with chlorhexidine gluconate and an encasing layer comprising two polymers as follows. No primer layer was included in these catheters. As a control, mylar pieces without an encasing layer (i.e., containing only an aqueous drug layer) were compared.

A. Chlorhexidine Gluconate Layer:

A 20 weight % aqueous solution of chlorhexidine gluconate (Sigma Aldrich, St. Louis, Mo.) was spray coated on mylar (3"×3" pieces, Grafix Dura-Lar™, 0.003 inch thickness) with a low volume low pressure EFD 7856-46SS sprayhead with Valvemate 2000 (Nordson EFD, East Providence, R.I.). 80 psi backing pressure was used, with a nozzle stroke setting of 12-14.5. The mylar piece was fixtured horizontally and the spray head was moved via an Exacta-Coat xyz plotter (Sonotek Corp, Milton, N.Y.) at 20 mm/sec in a 1 inch square pattern with a spray spacing of 10 mm at a distance of 1 inch above the mylar. The chlorhexidine gluconate aqueous solution was fed into the spray valve via a syringe pump at 0.2-0.4 ml/min. Once coated, the mylar piece was air dried in a fume hood for 24 hours at room temperature.

TABLE 4

| Encasing layer formulation mg/ml in hexane | | | | mg | mg | Elution profile into distilled water with $NaNO_3$, pH 7 Reported in mg Ag+/L | | | | | |
|---|---|---|---|---|---|---|---|---|---|---|---|
| PIB | PBMA | Photo-POMAS | PS-PEB-PS | $AgNO_3$ | Encasing layer | 15 min | Day 1 | Day 2 | Day 3 | Day 4 | Day 5 |
| 15 | | | | — | — | 507 | 51.2 | 5.4 | 1.4 | 3.9 | — |
| 30 | | | | 150.5 | 251.4 | 14 | 94.4 | 36.1 | 29.2 | 58.3 | 33.1 |
| 30 | | 5 | | 85.7 | 160.7 | 14.5 | 54 | 34.7 | 21.7 | 20.8 | 13.8 |
| 30 | | 15 | | 90 | 197.3 | 10.9 | 64.6 | 44.1 | 49.3 | 25.7 | 23.2 |
| 20 | | 5 | 20 | 107 | 261.9 | 5.9 | 47.3 | 59.1 | 26.2 | 25.3 | 15.8 |
| 20 | | | 20 | 91.9 | 103.1 | 7.0 | 46.1 | 37.4 | 45.6 | 19.2 | 23.9 |
| 10 | | 5 | 30 | 103.8 | 72.7 | 64.3 | 244 | 23.8 | 4.5 | 2.6 | 0.8 |
| | | | 100 | 84 | 52.9 | 186 | 613 | 87.1 | 8.6 | — | 4.7 |
| | 50 | | | — | — | 626 | 31.3 | 2.0 | 1.8 | 1.5 | — |
| 20 | 15 | | | — | — | 641 | 306 | 3.1 | 1.1 | 0.6 | |

B. Encasing Layer:

A solution of 24.6 mg/ml polyisobutylene ($M_w$ 4.2 million, BASF Ludwigshafen, Germany) and 8.2 mg/ml Photo-POMAS in hexane was prepared. Mylar pieces coated with chlorhexidine gluconate were dipcoated in the polyisobutylene:Photo-POMAS solution by inserting at 2 cm/sec. Pieces were dwelled in the solution for 10 seconds, then were extracted at 2.0 cm/sec. Coated pieces were air dried overnight at room temperature.

C. Slow Elution into Aqueous Solution:

Pieces of mylar coated above with conditions in Table 5 were individually placed in 50 ml conical vials with 45 ml of 1× phosphate buffered saline at 37° C. Chlorhexidine gluconate elution was monitored by UV absorbance at 254 nm over time on a Spectramax M2 (Molecular Devices, Sunnyvale, Calif.) and quantified against a calibration curve ($\epsilon_{254}$=42.813). At each daily time point the elution buffer was exchanged for a fresh 45 ml of 1× phosphate buffered saline. The mylar control contained no chlorhexidine gluconate (CHG). Results indicated CHG elution was controlled (both in terms of how quickly drug was released from the mylar, and in terms of total amount of drug released) when an encasing layer was included.

TABLE 5

| Sample | Stroke Volume | Inflow of solution from syringe pump | Elution of CHG in mg 2 hrs | Elution of CHG in mg 24 hrs | Elution of CHG in mg 48 hrs | Elution of CHG in mg 72 hrs |
|---|---|---|---|---|---|---|
| Mylar control | NA | NA | 0.01 | 0.01 | 0.02 | 0.02 |
| CHG no encasing layer control | 14.5 | 0.3 | 1.63 | 2.49 | 2.59 | 2.65 |
| CHG 1 | 15 | 0.4 | 0.18 | 0.95 | 1.22 | 1.36 |
| CHG 2 | 12 | 0.2 | 0.25 | 0.43 | 0.62 | 0.75 |

Example 9. Encasing Layer

Silicone tubing is coated with primer and silver nitrate as described in Example 1A and B. An encasing layer solution is made containing 30 mg/ml polyisobutylene (Mw 1-4 million, BASF, Ludwigshafen, Germany) and 15 mg/ml of derivatized poly(maleic anhydride-alt-1-octadecene)silane synthesized in Example 12 of US Patent Application "Coating Agents and Coated Articles" (Wen et al.) in hexane. After application of the primer layer and silver nitrate layer, the coated tubing is dipcoated in the encasing layer solution with an insertion rate of 2 cm/sec, 10 seconds dwell time, and 2 cm/sec extraction rate. The resulting coated tubing is air dried overnight protected from light.

The complete disclosure of all patents, patent applications, and publications cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The disclosure is not limited to the exact details shown and described, for variations obvious to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A drug eluting article comprising:
   a substrate and a multilayer coating, the multilayer coating comprising:
   a primer layer disposed on the substrate, the primer layer comprising a polymer that is a polymaleic acid derivative, one or more latent reactive groups that are pendent from the polymer, and one or more siloxane groups;
   a hydrophilic drug layer comprising a highly water soluble drug disposed on the primer layer; and
   a hydrophobic encasing layer disposed on the hydrophilic drug layer, the hydrophobic encasing layer comprising the polymaleic acid derivative polymer of the primer layer, a polyisobutylene polymer, or a mixture of the polymaleic acid derivative polymer and the polyisobutylene polymer,
   wherein the highly water soluble drug is not mixed with binder material within the hydrophilic drug layer, and wherein the multilayer coating shows controlled release of the drug after the multilayer coating has been punctured or sliced.

2. The drug eluting article according to claim 1 wherein the substrate comprises silicone.

3. The drug eluting article according to claim 1 wherein the polymer of the hydrophobic encasing layer comprises one or more noncovalent linking groups that are pendent from the polymer, the noncovalent linking groups selected to interact with the substrate.

4. The drug eluting article according to claim 1 wherein the hydrophobic encasing layer does not include latent reactive groups.

5. The drug eluting article according to claim 1 wherein the ratio of hydrophobic encasing layer to highly water soluble drug is at least 0.7 to 1.

6. The drug eluting article according to claim 1 wherein the hydrophobic encasing layer is present in at least a substantially equal weight amount as the highly water soluble drug.

7. The drug eluting article according to claim 1 wherein the weight ratio of hydrophobic encasing layer to highly water soluble drug is in a range of about 2:1 to about 2.5:1.

8. The drug eluting article according to claim 1 wherein the highly water soluble drug comprises silver nitrate, chlorhexidine gluconate, or a combination thereof.

9. The drug eluting article according to claim 1 wherein the one or more latent reactive groups comprise a photoreactive group.

10. The drug eluting article according to claim 1 wherein the polymaleic acid derivative comprises a poly(alkane-co-maleic acid).

11. A method of forming a multilayer coating on a substrate, the method comprising steps of:
   disposing a primer composition on the substrate, the primer composition comprising a polymer that is a polymaleic acid derivative, one or more latent reactive groups that are pendent from the polymaleic acid derivative, and one or more silicone affinity groups;
   curing the primer composition to form a primer layer;
   coating an aqueous solution of a highly water soluble drug onto the primer layer to form a highly water soluble drug layer, the highly water soluble drug layer having a first weight value;
   coating a non-aqueous solution of an encasing polymer onto the highly water soluble drug layer to form an encasing layer, the encasing layer having a second weight value, wherein the encasing polymer is provided in a solvent that is not soluble with the drug layer, and wherein the drug layer of the formed multilayer coating does not contain binder material.

12. The method according to claim 11 wherein the second weight value is greater than or equal to the first weight value.

13. The method according to claim 11 wherein the non-aqueous solution comprises a $C_5$-$C_{12}$ alkane and an encasing polymer that is at least soluble in the $C_5$-$C_{12}$ alkane.

14. The method according to claim 11 wherein the non-aqueous solution comprises polyisobutylene.

15. The method according to claim 11 wherein the non-aqueous solution comprises a polymaleic acid derivative, a polystyrene block copolymer, or a combination of these.

16. The method according to claim 11 wherein one or more latent reactive groups comprise photoreactive groups, and the silicone affinity groups comprise siloxane groups.

17. The method according to claim 11 wherein the substrate comprises silicone.

18. The method according to claim 11 wherein the highly water soluble drug comprises silver nitrate, chlorhexidine gluconate, or a combination thereof.

19. The drug eluting article according to claim 1 wherein the hydrophilic drug layer comprises drug in an amount of 95% by weight or greater.

* * * * *

UNITED STATES PATENT AND TRADEMARK OFFICE
CERTIFICATE OF CORRECTION

PATENT NO. : 9,814,805 B2  
APPLICATION NO. : 14/786842  
DATED : November 14, 2017  
INVENTOR(S) : Taton et al.

Page 1 of 1

It is certified that error appears in the above-identified patent and that said Letters Patent is hereby corrected as shown below:

On the Title Page

At (72) Inventors, "Lawin Laurie" should read -- Laurie Lawin --.

Signed and Sealed this  
Nineteenth Day of December, 2017

Joseph Matal  
*Performing the Functions and Duties of the*  
*Under Secretary of Commerce for Intellectual Property and*  
*Director of the United States Patent and Trademark Office*